US009031543B2

(12) United States Patent
Lee

(10) Patent No.: US 9,031,543 B2
(45) Date of Patent: May 12, 2015

(54) VISUALIZATION OF NETWORK MEMBERS BASED ON LOCATION AND DIRECTION

(75) Inventor: Arthur C. Lee, San Diego, CA (US)

(73) Assignee: QUALCOMM Incorporated, San Diego, CA (US)

(*) Notice: Subject to any disclaimer, the term of this patent is extended or adjusted under 35 U.S.C. 154(b) by 232 days.

(21) Appl. No.: 13/489,526

(22) Filed: Jun. 6, 2012

(65) Prior Publication Data

US 2013/0331130 A1    Dec. 12, 2013

(51) Int. Cl.
*H04M 3/42* (2006.01)
*H04W 24/00* (2009.01)
(Continued)

(52) U.S. Cl.
CPC ............ *H04W 4/08* (2013.01); *H04L 12/18* (2013.01); *H04M 3/42348* (2013.01); *H04M 3/563* (2013.01); *H04W 64/006* (2013.01); *H04M 2201/38* (2013.01); *H04M 2203/2044* (2013.01); *H04M 2207/18* (2013.01); *H04M 2242/30* (2013.01); *H04M 2250/12* (2013.01); *H04M 2250/22* (2013.01); *H04M 2250/66* (2013.01); *H04M 2203/359* (2013.01); *H04W 4/023* (2013.01)

(58) Field of Classification Search
CPC ....... H04W 4/02; H04W 4/023; H04W 4/025; H04W 4/026; H04W 4/04; H04W 4/043; H04W 4/206; H04L 67/18; H04M 1/72572
USPC .......................... 455/414.1–414.3, 456.1–459
See application file for complete search history.

(56) References Cited

U.S. PATENT DOCUMENTS 7,231,205 B2   6/2007   Guyot et al.
7,847,815 B2   12/2010  Patel et al.
(Continued)

FOREIGN PATENT DOCUMENTS

EP    2237533 A1    10/2010
GB    2380080 A     3/2003
(Continued)

OTHER PUBLICATIONS

International Search Report and Written Opinion—PCT/US2013/044206—ISA/EPO—Sep. 3, 2013.
(Continued)

*Primary Examiner* — George Eng
*Assistant Examiner* — Nam Huynh
(74) *Attorney, Agent, or Firm* — Raphael Freiwirth

(57) ABSTRACT

Methods, devices and systems enable efficient organizations of group communications on a mobile device. The mobile device may be configured to receive location information from other mobile devices in a communication system, determine the current location and orientation of the mobile device, determine directions and distances from the mobile device to each of the other mobile devices, and generate a first-person perspective and/or top-down perspective display showing relative locations of the other mobile devices. Other multiple mobile devices may be represented in the display as images (e.g., icons, avatars, directional indicators, etc.). The display may provide a user interface to enable a user to quickly organize other mobile devices into groups and initiate group communications with some of the other mobile devices. The mobile device may be configured to group the displayed images into one or more communication units and establish communication links with mobile devices in the communication units.

20 Claims, 11 Drawing Sheets

(51) Int. Cl.
*H04W 4/08* (2009.01)
*H04M 3/56* (2006.01)
*H04W 64/00* (2009.01)
*H04W 4/02* (2009.01)
*H04L 12/18* (2006.01)

(56) References Cited

U.S. PATENT DOCUMENTS

| | | |
|---|---|---|
| 2002/0183052 A1 | 12/2002 | Tachikawa |
| 2006/0063539 A1* | 3/2006 | Beyer .................. 455/456.3 |
| 2006/0259755 A1 | 11/2006 | Kenoyer |
| 2007/0004426 A1 | 1/2007 | Pfleging et al. |
| 2007/0078965 A1 | 4/2007 | Shimamura et al. |
| 2007/0117576 A1 | 5/2007 | Huston |
| 2007/0142091 A1* | 6/2007 | Gasborro et al. ............ 455/566 |
| 2007/0188598 A1 | 8/2007 | Kenoyer |
| 2008/0076418 A1 | 3/2008 | Beyer, Jr. |
| 2008/0132243 A1 | 6/2008 | Spalink et al. |
| 2009/0268009 A1 | 10/2009 | Oya |
| 2010/0149305 A1 | 6/2010 | Catchpole et al. |
| 2011/0074911 A1 | 3/2011 | Khouri et al. |
| 2014/0055553 A1 | 2/2014 | Lee et al. |

FOREIGN PATENT DOCUMENTS

| | | |
|---|---|---|
| WO | 2010022756 A1 | 3/2010 |
| WO | 2012046425 A1 | 4/2012 |

OTHER PUBLICATIONS

Partial International Search Report—PCT/US2013/044206—ISA/EPO—Jul. 18, 2013.

* cited by examiner

VISUALIZATION OF NETWORK MEMBERS BASED ON LOCATION AND DIRECTION

BACKGROUND

Cellular and wireless communication technologies have seen explosive growth over the past several years. Wireless service providers now offer a wide array of features and services that provide their users with unprecedented levels of access to information, resources and communications. To keep pace with these service enhancements, mobile electronic devices (e.g., cellular phones, tablets, laptops, etc.) have become more feature rich, and now commonly include global positioning system (GPS) receivers, sensors, and many other components for connecting users to friends, work, leisure activities and entertainment. However, despite these recent advancements, mobile devices remain lacking in their ability to perform group communications (e.g., one-to-many, many-to-many, etc.) efficiently and in a user friendly manner. As mobile devices and technologies continue to grow in popularity and use, improving group communication capabilities of mobile devices is expected to become an important and challenging design criterion for mobile device designers.

SUMMARY

The various embodiments may include methods for performing group communications by receiving, on a mobile device, location information associated with a plurality of other mobile devices that are members of a communication system, determining a location of the mobile device, determining an orientation of the mobile device, determining a relative distance between the mobile device and each of the plurality of other mobile devices based on the determined location of the mobile device and the location information received from the plurality of other mobile devices, determining a relative direction of each of the plurality of other mobile devices with respect to the determined orientation of the mobile device, generating on an electronic display of the mobile device images representative of each of the plurality of other mobile devices based on the determined relative distance and the determined relative direction, receiving a user input on the display, grouping two or more of the generated images into a communication unit in response to the user input, and establishing group communications with the communication unit.

In an embodiment, the method may include associating a direction vector with the determined orientation of the mobile device, and identifying at least one of the plurality of other mobile devices located along the direction vector, in which generating on an electronic display of the mobile device images representative of each of the plurality of other mobile devices based on the determined relative distance and the determined relative direction may include generating a first-person perspective display in which only mobile devices in the plurality of other mobile devices that are located along the direction vector are represented by images. In a further embodiment, generating on an electronic display of the mobile device images representative of each of the plurality of other mobile devices based on the determined relative distance and the determined relative direction may include generating the images in sizes indicative of the determined relative distance and the determined relative direction.

In a further embodiment, the method may include determining whether the mobile device has changed orientation, associating a new direction vector with the changed orientation of the mobile device, and generating an updated first-person perspective display in which only mobile devices in the plurality of other mobile devices located along the new direction vector are represented by an image. In a further embodiment, the mobile device may be a member of a communication group and images of devices that are members of the communication group are displayed differently from images of devices that are not members of the communication group. In a further embodiment, the mobile device may be a member of a communication group and only the images of devices in the communication group are displayed in the first-person perspective display.

The various embodiments may also include methods of generating a display on a mobile device that is a member of a communication system by including receiving location information associated with each communication device in the communication system, determining a location of the mobile device, determining a distance between the mobile device and each communication device in the communication system, generating a first-person perspective display in which each communication device in the communication system may be represented by an image based on the determined distance between the mobile device and the communication device associated with that image, determining whether the mobile device has changed orientation to a horizontal position, and generating a top-down perspective display in which a first icon associated with the mobile device appears at a center of the top-down perspective display and each of the devices may be represented by an image positioned around the first icon associated with the mobile device based on relative positions of each of the communication device in the communication system.

Further embodiments may include a computing device having a processor configured with processor-executable instructions to perform various operations corresponding to the methods discussed above.

Further embodiments may include a computing device that may include various means for performing functions corresponding to the method operations discussed above.

Further embodiments may include a non-transitory processor-readable storage medium having stored thereon processor-executable instructions configured to cause a processor to perform various operations corresponding to the method operations discussed above.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
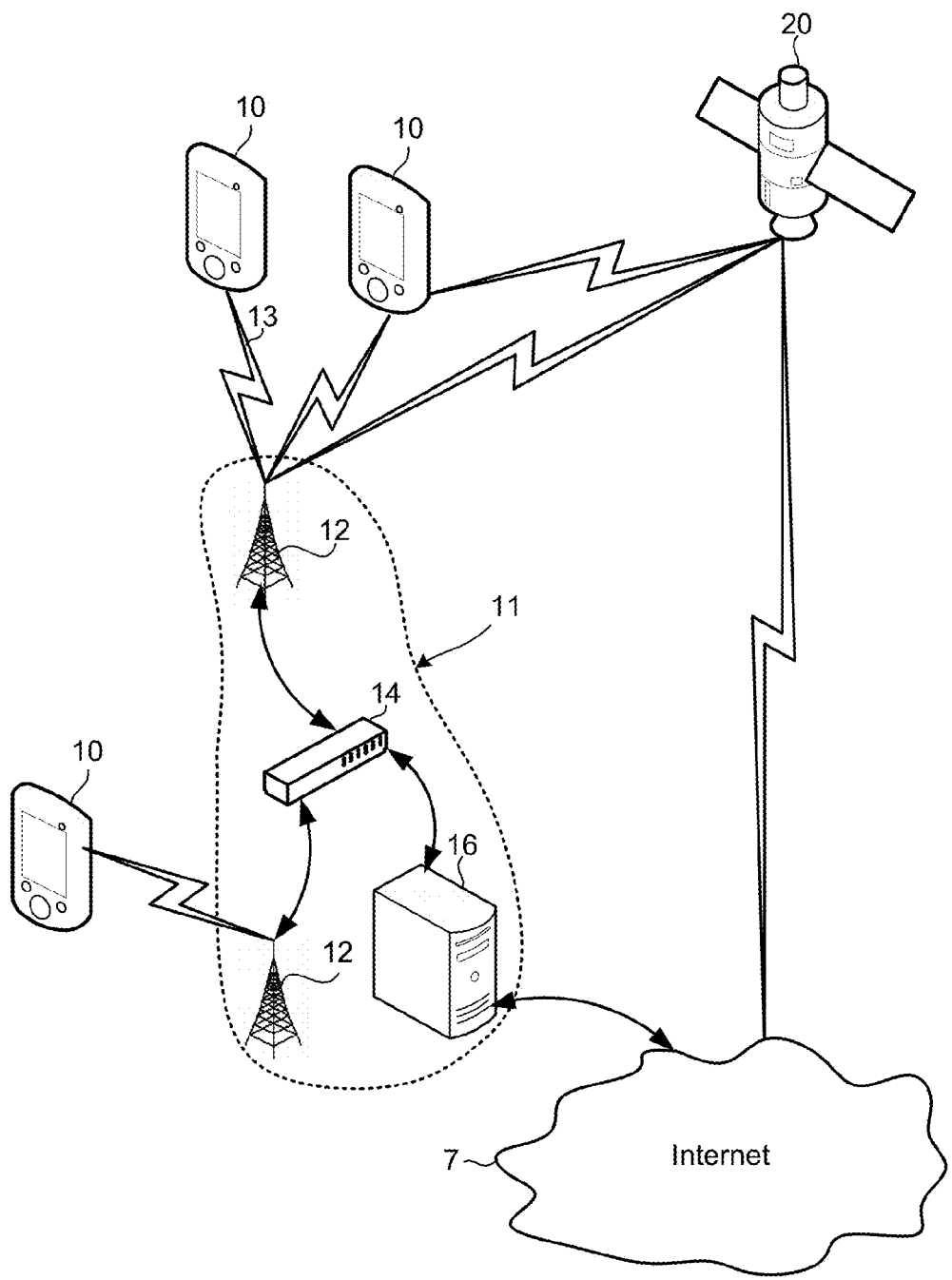
FIG. 1 is a communication system block diagram illustrating a cellular communication system suitable for use in an embodiment.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The term "computing device" is used generically herein to refer to any one or all of servers, personal computers, mobile devices, cellular telephones, tablet computers, laptop computers, netbooks, ultrabooks, palm-top computers, personal data assistants (PDA's), wireless electronic mail receivers, multimedia Internet enabled cellular telephones, Global Positioning System (GPS) receivers, wireless gaming controllers, and similar personal electronic devices which include a programmable processor and communications circuitry for sending and receiving wireless communication signals.

The terms "mobile device," "wireless device" and "user equipment" (UE) may be used interchangeably and refer to any one of various cellular telephones, smartphones (e.g., iPhone®), personal data assistants (PDA's), palm-top computers, tablet computers (e.g., iPad®), laptop computers, wireless electronic mail receivers (e.g., Blackberry®), VoIP phones, multimedia/Internet enabled cellular telephones, gaming consoles, and similar electronic devices that include a programmable processor and are capable of sending and receiving wireless communication signals. While the various aspects are particularly useful in mobile devices, such as cellular telephones, the aspects are generally useful in any computing device that includes communications circuitry for sending and receiving wireless communication signals.

As mentioned above, mobile devices remain lacking in their ability to perform group communications efficiently and in a user friendly manner. For example, various existing group communication systems (e.g., push-to-talk systems) may enable a mobile device to receive information about the availability and/or the network addresses of other mobile devices, but lack the ability to communicate relative and absolute location information for use by other mobile devices. Likewise, location-aware mobile software applications (e.g., "Find my Friends" on Apple® for iOS 5, Google® Latitude, etc.) may enable a mobile device user to view the geographical position of other mobile devices, but lack the ability to use such information to perform group-based communications. Moreover, existing location-aware software applications simply locate and display the locations of the users on a map, and do not provide a rich and user-friendly interface that enables users to efficiently group users and/or establish communications links with groups of users. The various embodiments overcome these and other limitations of existing solutions by collecting location information from a multiple mobile devices, and displaying the locations of the other mobile devices on an interactive graphical user interface (GUI) of the mobile device in a first-person perspective and/or a top-down perspective such that the user may quickly organize the other mobile device users into groups and initiate group communications with the other mobile device users or groups of mobile device users.

The various embodiments include methods, devices, and systems for visually locating and clustering mobile device users into groups, and establishing group communication links with members in the visually identified groups. Various embodiments may include a mobile device configured to present a first person perspective user interface that displays the relative locations/positions of other mobile devices relative to the location/position of the mobile device. Various embodiments may include a mobile device configured to present a top-down perspective user interface that displays the relative locations of other mobile devices in multiple directions (e.g., within a diameter) relative to the location/position of the mobile device.

In an embodiment, a mobile device may be configured to switch into the first person perspective when the mobile device is moved into an upright or vertical position (e.g., perpendicular to the ground, perpendicular to the gradient of the gravity, not parallel to the ground, etc.), and into the top-down perspective when the mobile device is moved into a horizontal or laid down position (e.g., parallel to the ground, not in a vertical position, etc.). Mobile device users may employ any combination of the first person perspective and the top-down perspective to locate other mobile device users and initiate group communications with the located mobile device users.

The various embodiments may be implemented within a variety of communication systems, such as a cellular telephone network, an example of which is illustrated in FIG. 1. A typical cellular telephone network 11 includes a plurality of cellular base stations 12 coupled to a network operations center 14, which operates to connect voice and data calls between mobile devices 10 (e.g., mobile phones) and other network destinations, such as via telephone land lines (e.g., a POTS network, not shown) and the Internet 7. Communications between the mobile devices 10 and the cellular telephone network 11 may be accomplished via two-way wireless communication links 13, such as 4G, 3G, CDMA, TDMA, and other cellular telephone communication technologies. The network 11 may also include one or more servers 16 coupled to or within the network operations center 14 that provide connections to the Internet 7 and/or are used to perform various operations, such as processing the signals to remove background noise. The network 11 may communicate with geo-spatial positioning and navigation satellite systems 20 to identify the geographic position of the mobile devices 10.

Figure 2:
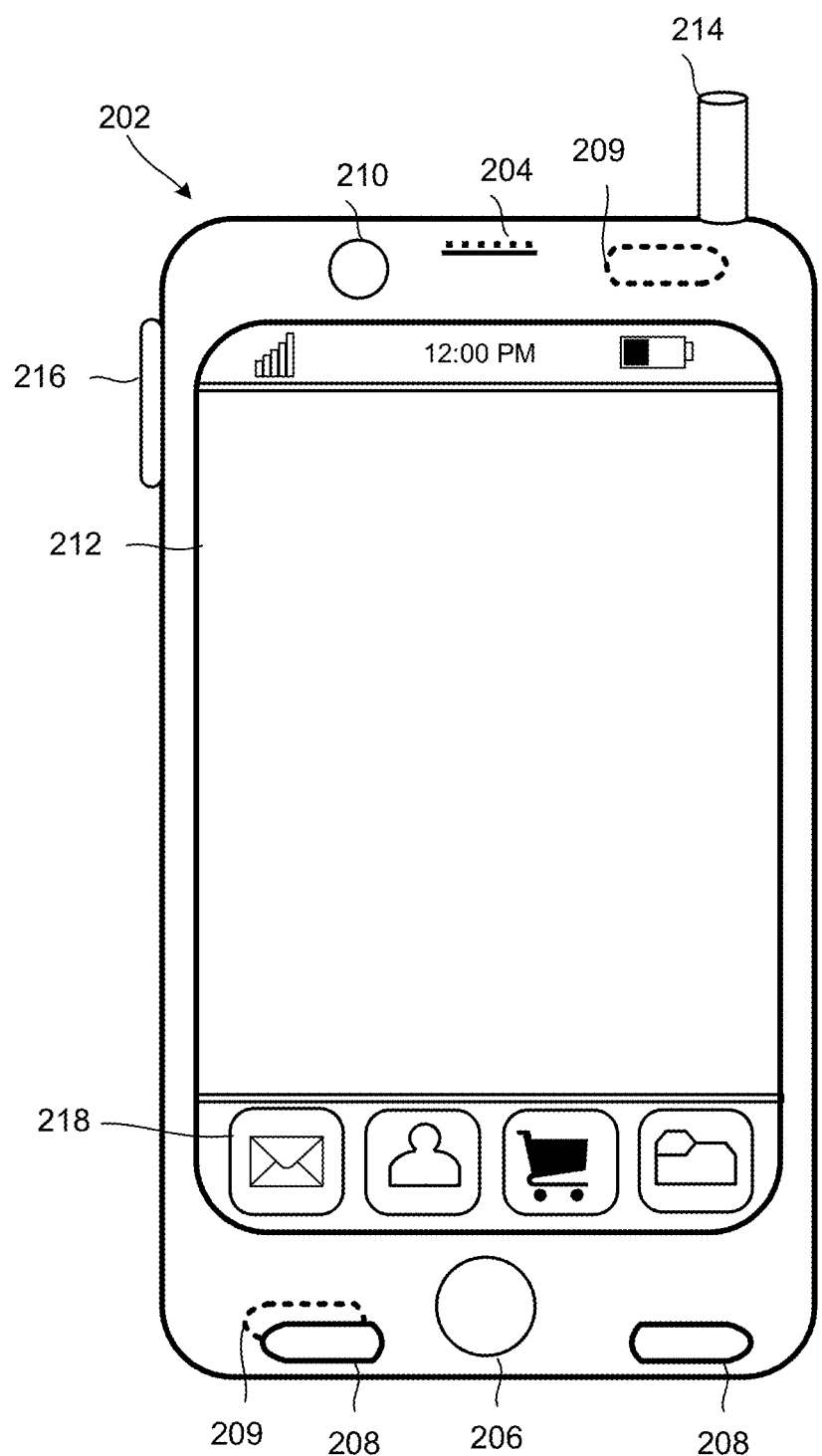
FIG. 2 is an illustration of a mobile communication device showing a user interface that may be used in accordance with the various embodiments.

FIG. 2 illustrates sample components of a mobile device in the form of a smartphone 202 that may be used with the various embodiments. The smartphone 202 may include a speaker 204, user interface elements 206, 216, 218 for receiving user inputs, one or more microphones and/or microphone arrays 208 for capturing sounds, one or more sensors 209 for monitoring physical conditions (e.g., location, direction, motion, orientation, vibration, pressure, etc.), an antenna 214 for sending and receiving electromagnetic radiation, a camera 210, an electronic display 212, and other well known components (e.g., accelerometer, etc.) of modern electronic devices (e.g., electronic personal trainers, smartphones, mobile gaming consoles, etc.). The user interface elements 216, 218 (e.g., buttons, icons, etc.) may be implemented as hard key buttons, soft key buttons, as touch keys, or any other way of receiving user input. The phone 202 may include a processor and memory for receiving and executing software applications transmitted from an application download server (e.g., Apple® App Store server).

The phone 202 may also include a geo-spatial positioning and navigation system. For example, the phone 202 may include a GPS receiver configured to receive GPS signals from GPS satellites to determine the geographic position of the phone 202. In various embodiments, the phone 202 may further include other components for determining the geographic position of the phone 202, such as resources for determining the radio signal delays (e.g., with respect to cell-phone towers and/or cell sites), performing trilateration and/or multilateration operations, identifying proximity to known networks (e.g., Bluetooth® networks, WLAN networks, WiFi, etc.), and/or for implementing other known technologies for identifying a geographic location of a mobile device. The phone 202 may also include other sensors/components for collecting other types of physical conditions, such as information regarding the user's current movements (e.g., whether the user is currently traveling, exercising, stationary, etc.) and the orientation of the phone 202.

Software installed on the phone 202 may communicate (transmit, broadcast, etc.) location information identifying the location of the phone 202 to other mobile devices and/or receive location information from the other mobile devices. In various embodiments, the location information may be communicated to other mobile devices via a direct communication link between the devices, via broadcast, through a central server, or via any other known mobile or wireless communication technologies. The location information may be sent to the other mobile devices periodically, at set intervals, and/or on demand. The location information may be stored in a memory on the mobile device 202, on another communication device, on a server, on the Internet (e.g., in "the cloud"), or on any combination thereof.

As mentioned above, existing group communication systems generally lack the ability to communicate relative and absolute location information for use by other mobile devices. Also, existing group communication systems and location-aware mobile software applications lack the ability to use location information to perform group-based communications in a user friendly manner. Various embodiments overcome these and other limitations of existing solutions by collecting location information from a multiple mobile devices, and displaying the locations of the other mobile devices on an interactive graphical user interface (GUI) of the mobile device that enables the user to quickly organize users into groups and initiate group communications with a single operation.

In an embodiment, the mobile device may be configured to function as a virtual viewer (or "X-ray" viewer) by, for example, displaying icons/avatars representative of other mobile devices that are positioned along the direction that the mobile device is facing (e.g., as determined by an orientation sensor of the mobile device). The mobile device may leverage one or more mobile device sensors (e.g., accelerometers, etc.) to identify motion and/or changes in the "facing direction" of the mobile device, and update the interactive graphical user interface (GUI) to display avatars of user devices that are positioned along the new direction that the mobile device is facing. The interactive GUI may display the avatars in sizes consistent with the relative distances between the user's mobile device and the other mobile devices (the displayed avatars of closer mobile devices are larger than the displayed avatars of more distant mobile devices). The interactive GUI may receive user inputs for organizing the displayed avatars into groups (e.g., by receiving a touch screen input drawing a circle around two or more avatars, etc.), and for selecting displayed avatars or groups of avatars (e.g., by touching a displayed avatar or circle). The selection of a displayed avatar, or group of avatars, may initiate communications between the mobile device and other mobile devices corresponding to the selected avatars or groups.

In an embodiment, the mobile device may be configured to display the locations of the other mobile devices in a top-down perspective (e.g., on a two dimensional map, radar screen, etc.), enabling the mobile device user to view icons/avatars representative of the other mobile devices located in multiple directions (e.g., within a diameter) at once. The mobile device may be configured to enable users to zoom in or out on the interactive GUI to view the other mobile device users over various distances, or as being closer or farther away. The interactive GUI may enable the mobile device user to create communication groups by, for example, drawing circles around multiple avatars or by specifying a radius or diameter within which all other mobile devices are to be selected. The interactive GUI may enable the mobile device user to add or remove members from the groups by, for example, pressing or actuating icons/avatars representative of the members to be added or removed.

In an embodiment, the mobile device may be configured to switch into the first person perspective when the mobile device is moved into an upright or vertical position (e.g., perpendicular to the ground, perpendicular to the gradient of the gravity, not parallel to the ground, etc.). In an embodiment, the mobile device may be configured to switch into the top-down perspective when the mobile device is moved into a horizontal or laid down position (e.g., parallel to the ground, not in a vertical position, etc.). In an embodiment, the mobile device may be configured to function in both the first-person perspective and top-down perspective. The mobile device may be configured to enable a mobile device user to transition between the two perspectives as desired. For example, the mobile device may be configured to enable a user to locate other mobile device users in the first-person perspective, and to switch into the top-down perspective to initiate a group call with the located mobile device users.

In an embodiment, the mobile device may be configured to dynamically update and/or indicate visual representations of mobile devices (e.g., icons, avatars, etc.) based on updates to mobile device user activities and/or statuses (e.g., the user is jogging, traveling in a car, sleeping, busy, available, etc.).

Figure 3A:
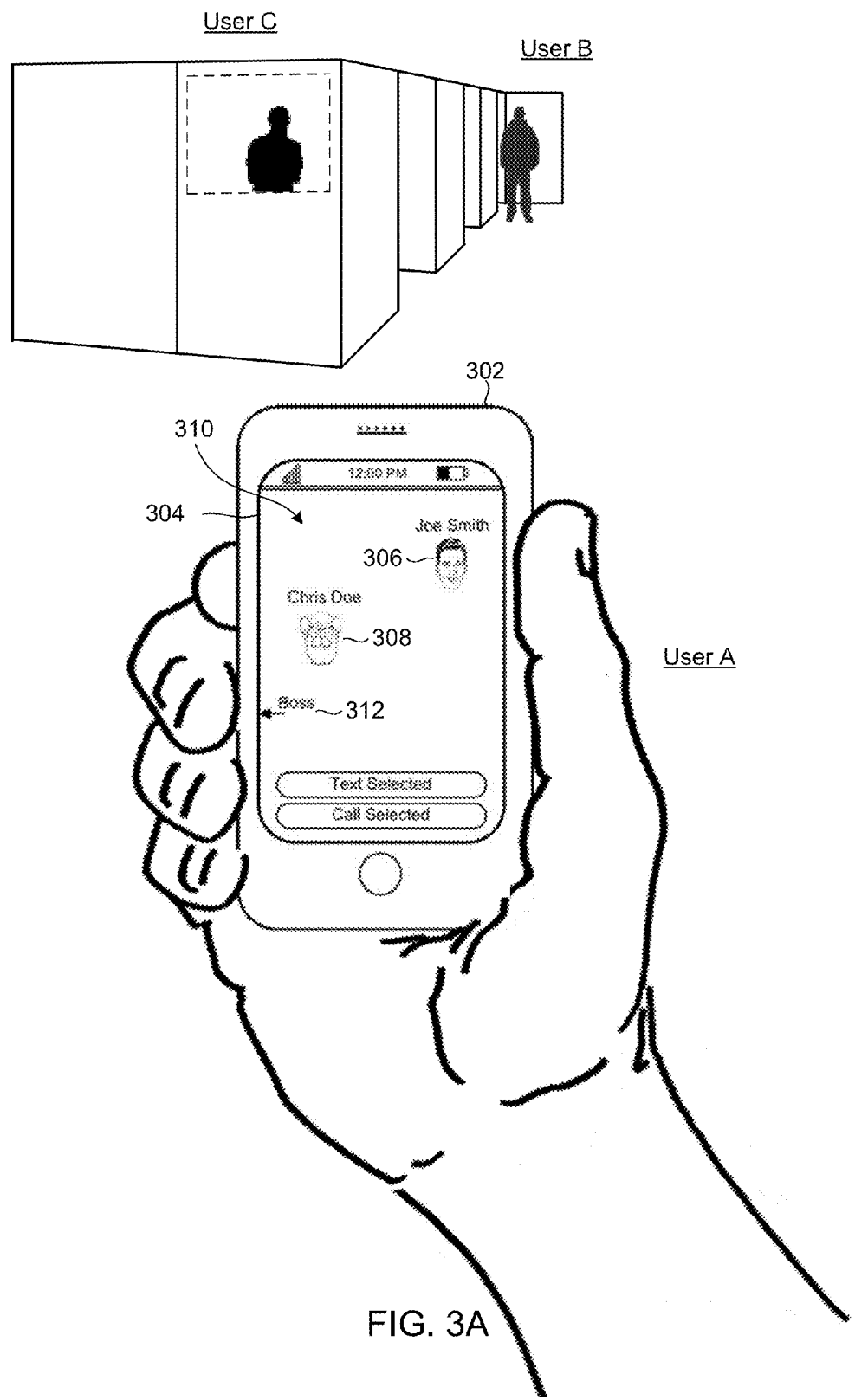
FIGS. 3A-B are illustrations of a mobile communication device having an interactive graphical user interface configured to display images representative of other mobile devices in a first-person perspective according to an embodiment.
Figure 3B:
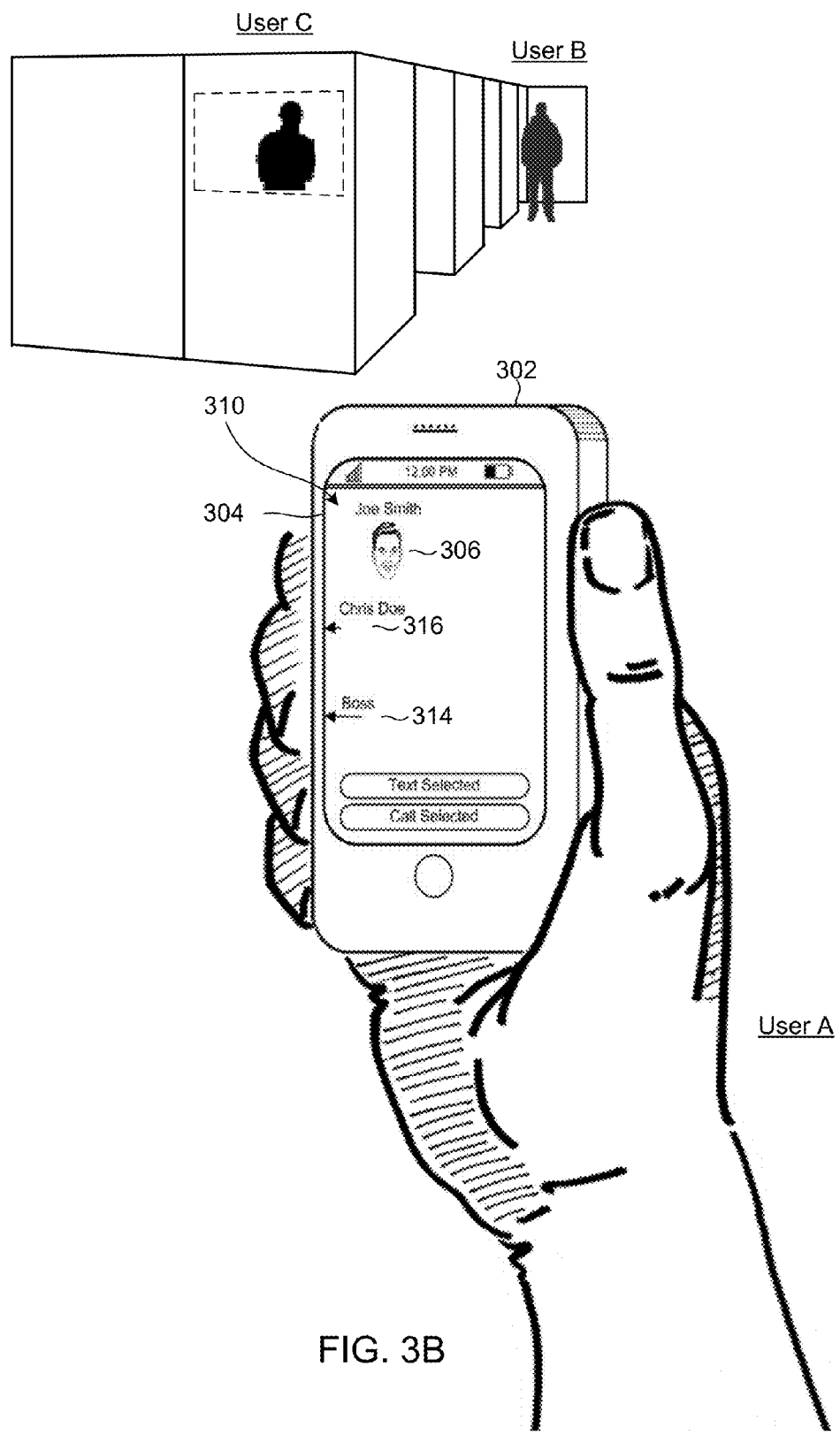

FIGS. 3A-B are illustrations of a mobile device 302 having an interactive graphical user interface 304 configured to display icons/avatars 306, 308 representative of other mobile devices physically located in a direction the mobile device is facing (herein "facing direction") in a first-person perspective according to an embodiment. FIG. 3A illustrates example content 310 that may be displayed on the interactive graphical user interface 304 when the mobile device is held in a vertical position by User A so that User B and User C are physically located in a facing direction of the mobile device. FIG. 3B illustrates example updates to the displayed content 310 after User A pans the mobile device 302 to the right such that User C is no longer physically located in the facing direction of the mobile device.

In the example illustrated in FIG. 3A, Users A, B, and C each have mobile devices on or near their person, and the mobile device is held in a vertical position by User A and oriented in the direction of User B and User C. User B is visible to User A's naked eye, whereas User C is behind a cubical wall. Another user ("Boss") is not in the facing direction of the mobile device and not visible to the User A's naked eye.

The mobile devices of Users B and C may gather and publish location information identifying their physical locations. The mobile device 302 may receive the location information published by each of these mobile devices, and use the received location information to display avatars/icons 306, 308 that are representative of Users B and C on the interactive graphical user interface 304. In this manner, the mobile device 302 may locate individuals (via their mobile devices) regardless of whether or not the individuals are visible.

In an embodiment, mobile devices that are members of the group communication system but are not physically located along the direction that the mobile device is facing (e.g., "Boss") may be represented by a directional indicator 312 instead of an avatar. The directional indicator 312 may point in the direction of the physical location of the represented mobile device ("Boss"). The size and/or length of the directional indicator 312 may be indicative of the relative distance between the mobile device 302 and the represented mobile device ("Boss"). The directional indicator 312 may be displayed such that it identifies a direction in which the mobile device 302 must be panned in order to view an avatar associated with the represented mobile device. In an embodiment, the directional indicator 312 may identify the directions of users in special calling groups selected by USER A.

As mentioned above, the interactive graphical user interface 304 of the mobile device 302 may display avatars/icons 306, 308 that are representative of mobile devices located along the facing direction of the mobile device 302. In various embodiments, the mobile device 302 may retrieve these icons/avatars 306, 308 from a device memory and/or receive the icons/avatars 306, 308 from the other mobile devices. In an embodiment, the icons/avatars 306, 308 may be displayed in different sizes and in different positions on the electronic display. In an embodiment, the icons/avatars 306, 308 may be displayed such that they are representative of the relative positions, locations, and/or distances between User A and Users B and C. For example, the interactive graphical user interface 304 may display a larger avatar for User C and a smaller avatar for User B to indicate that the distance between User C and User A is less than the distance between User B and User A. In an embodiment, the avatar sizes may be computed on a logarithmic scale so that users in the group communication system who are extremely far away may still be visible on the interactive graphical user interface 304.

In an embodiment, the mobile device 302 may include various sensors (e.g., accelerometers, etc.) for detecting movement, panning, and/or changes in the orientation or facing direction of the mobile device 302. Information collected from these sensors may be used by the mobile device 302 to compute/update one or more directional vectors, which may include information for identifying the position/orientation of the mobile device 302 relative to other mobile devices. In an embodiment, the mobile device 302 may be configured to update the direction vectors and visual outputs in a real-time, continuous, manner. For example, the mobile device 302 may be configured such that each time the mobile device 302 is panned, a new directional vector is computed and the displayed content 310 is updated to include avatars that are representative of user devices physically located along the newly computed directional vector.

FIG. 3B illustrates example updates to the displayed content 310 after User A pans the mobile device 302 to the right so that User C is no longer in the facing direction of the mobile device 302. That is, FIG. 3B illustrates an example in which the mobile device 302 is held in a vertical position by User A in the direction of User B so that User C and "Boss" are not physically located in the facing direction of the mobile device. In the illustrated example of FIG. 3B, the interactive graphical user interface 304 displays an icon/avatar 306 representative of User B because User B is still positioned along the facing direction of the mobile device 302. User C and "Boss" are represented by directional indicators 314, 316 because User C and "Boss" are not physically located along the facing direction of the mobile device. The size and/or length of the directional indicators 314, 316 may represent the relative distances and/or directions of User C and "Boss." For example, User C may be represented by a shorter directional indicator 316 and "Boss" may be represented by a longer directional indicator 314 to indicate that User C is physically closer to User A (e.g., in distance, orientation, etc.) than "Boss" is to User A.

As discussed above, various embodiments may include an interactive graphical user interface 304 configured to display icons, avatars, and directional indicators (collectively user images) representative of users in a group communication system. The interactive graphical user interface 304 may display the user images graphically and enable users to interact with the displayed content 310 to perform group communications. For example, the interactive graphical user interface 304 may enable users to grab and drag two or more user images together to create groups, draw circles around displayed user images to create groups, and enable users to initiate group communications by selecting user images or groups of images. In this manner, the various embodiments may simplify the initiation of group communications and/or the selection of users with which to initiate group communications.

In an embodiment, the interactive graphical user interface 304 may be configured to enable users to anchor avatars so that mobile devices corresponding to the anchored avatars are always represented on the electronic display of the user's mobile device regardless of the facing direction of the mobile device. For example, the interactive graphical user interface 304 may display the anchored avatars when their corresponding mobile devices are in the facing direction of the phone, and display directional indicators when their corresponding mobile devices are not in the facing direction of the phone. The directional indicators may be displayed such that they are indicative of the direction to pan the user device to view the anchored avatar.

Various embodiments may be best understood by the following sample use cases associated with the first-person perspective graphical display.

In a first use case, the primary mobile device user may be a construction site FOREMAN having two employees USER A and USER B. USER A may initiate a push-to-talk call with FOREMAN to inquire where construction materials are to be unloaded. FOREMAN may desire that the construction materials be unloaded near USER B, but may not be able to view USER B with his naked eye. FOREMAN may pan his/her mobile device around the job site until USER B is located, and an avatar representative of USER B may be displayed on the primary mobile device. The displayed avatar may identify how far away USER B is from FOREMAN and USER A. FOREMAN may instruct USER A to unload the construction materials in the identified location of USER B. FOREMAN may also instruct USER A to pan USER A's device in the identified direction of the USER B to find USER B, and to unload the construction materials in the vicinity of USER B.

In a second use case, the primary mobile device user may be an office EMPLOYEE on a company-wide international conference call from his/her office in San Diego. EMPLOYEE may recognize that answers to questions raised during the conference call require the participation of two people in a San Francisco office and three people in a China office, none of which are currently participating in the conference call. EMPLOYEE may pan his/her phone North to locate the people in the San Francisco office that EMPLOYEE believes are capable of providing answers to the questions raised during the conference call. EMPLOYEE may select the identified individuals by tapping on their displayed avatars. Likewise, EMPLOYEE may pan his/her phone down (e.g., towards the ground) to locate the people in the China office, and select the identified individuals by tapping on their displayed avatars. EMPLOYEE may then send all the selected individuals a group message requesting their participation in a group communication to provide answers to the questions raised during the conference call. The group message may be sent by, for example, tapping on the selected group and pressing a "send text" button. Upon receiving responses to the group message, EMPLOYEE may create a new group that includes the five located individuals (i.e., two people from San Francisco and two people from China), EMPLOYEE, and other individuals participating in the conference call. EMPLOYEE may establish group communication links (e.g., a new teleconference) with the members in the newly created group by, for example, tapping on the selected group and pressing a "call" button.

In a third use case, the primary mobile device user may be an office EMPLOYEE that has initiated a conference call with multiple members of his/her company. Upon determining that two of the multiple members participating in the conference call should be removed from the call, EMPLOYEE may pan his/her mobile device around to identify the relative location of the two participants with respect to the location of EMPLOYEE. EMPLOYEE may remove the two members from the call by selecting their avatars and flicking the selected avatars off the screen. In an embodiment, EMPLOYEE may have (exclusive) privileges for adding and/or removing members from the call, as may be the case when the EMPLOYEE initiated the call, the EMPLOYEE is a manager that has been granted such privileges, etc.).

In a fourth use case, the primary mobile device user may be an office WORKER participating in a push-to-talk call initiated by COWORKER located on the floor below WORKER. Upon determining that WORKER cannot answer the questions raised by COWORKER, WORKER may quickly pan the primary mobile device to identify the physical location of a project LEADER's office, which the WORKER knows is directly above (i.e., on the floor above) the WORKER. For example, WORKER may hold the primary mobile device up to the fluorescent lights to determine whether LEADER is in his office. Upon determining that LEADER is in his office (e.g., via LEADER's avatar being displayed on the screen), WORKER may select LEADER's avatar, anchor the selected avatar to the screen, pan the primary mobile device back toward the direction of COWORKER, and drag LEADER's avatar on top of COWORKER to add LEADER to the push-to-talk call. In response, the primary mobile device may create an ad-hoc group involving COWORKER, LEADER, and WORKER. If WORKER then desires to add additional people to the group call, WORKER may drag the additional person onto either the image associated with COWORKER or the image associated with LEADER to add the additional person to the call.

In a fourth use case, the primary mobile device user may be a CHILD that has become separated from his/her PARENT. CHILD may select an option on the interactive graphical user interface of the primary mobile device to filter the displayed avatar such that only avatars corresponding to mobile devices in the "family group" are displayed. CHILD may slowly wave the primary mobile device around until PARENT is located. As CHILD moves in the direction of PARENT, the primary mobile device may enlarge the avatar corresponding to PARENT. Similarly, as CHILD moves away from PARENT, the primary mobile device may reduce the size of the avatar corresponding to PARENT.

In a fifth use case, the primary mobile device user may be a USER attending a concert with a FRIEND. USER may point the primary mobile device at FRIEND to view an avatar corresponding to FRIEND. USER may anchor the avatar corresponding to FRIEND (e.g., by pressing FRIEND's avatar for a couple seconds to bring up an options menu) such that the primary mobile device always displays the location of FRIEND's mobile device regardless of the facing direction of the primary mobile device. As USER moves around the concert hall, USER may view an arrow or indication pointing in the direction of FRIEND so that USER can quickly pan over to that direction to find FRIEND.

In a sixth use case, the primary mobile device user may be an office EMPLOYEE on a company-wide international conference call from his/her office in San Diego. EMPLOYEE may recognize that answers to questions raised during the conference call require the participation of two people in a San Francisco office and three people in a China office, none of which are currently participating in the conference call. EMPLOYEE may pan his/her phone North to locate the people in the San Francisco office that EMPLOYEE believes are capable of providing answers to the questions raised during the conference call. EMPLOYEE may select the identified individuals by tapping on their displayed avatars. Likewise, EMPLOYEE may pan his/her phone down (e.g., towards the ground) to locate the people in the China office, and select the identified individuals by tapping on their displayed avatars. EMPLOYEE may create a new group that includes the five located individuals (i.e., two people from San Francisco and two people from China), EMPLOYEE, and other individuals participating in the conference call. EMPLOYEE may establish group communication links (e.g., a new teleconference) with the members in the newly created group by, for example, tapping on the selected group and pressing a "call" button.

As mentioned above, in an embodiment, the mobile device may be configured to display the locations of the other mobile devices in a top-down perspective (e.g., on a two dimensional map, etc.) that enables the mobile device user to view icons/avatars representative of the other mobile devices located in multiple directions (e.g., within a diameter) at once. The top-down perspective also enables users to quickly establish/identify their position relative to other users.

Figure 4A:
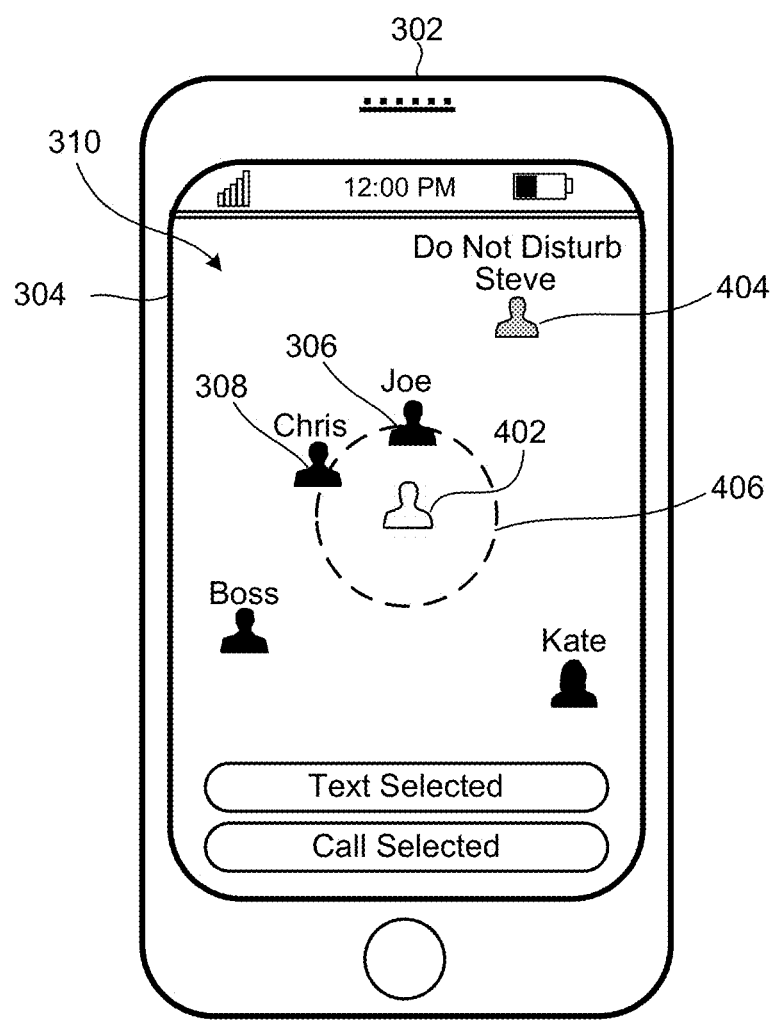
FIGS. 4A-B are illustrations of a mobile communication device having an interactive graphical user interface configured to display images representative of other mobile devices in a top-down perspective according to an embodiment.
Figure 4B:
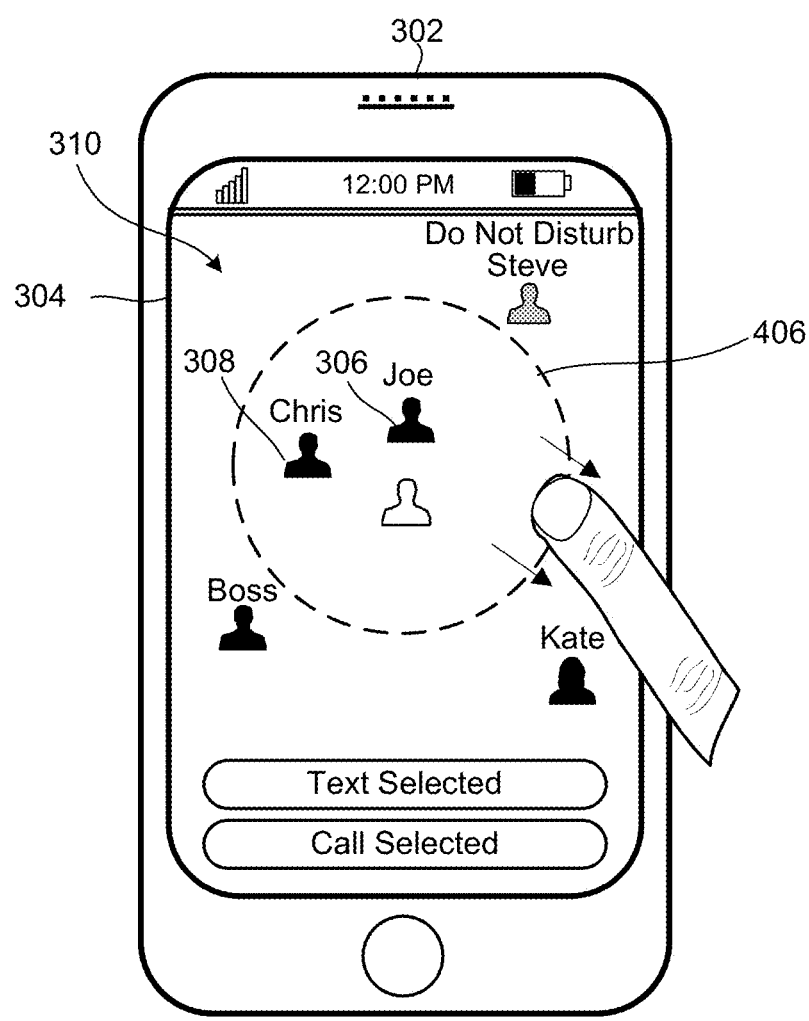

FIGS. 4A-B are illustrations of a mobile device 302 having an interactive graphical user interface 304 configured to display information in a top-down perspective according to an embodiment. In the examples illustrated in FIGS. 4A-B, the mobile device 302 may be configured to receive location information published by other mobile devices, and use the received location information to display avatars/icons 306, 308 that are representative of the physical locations of the other mobile devices on the interactive graphical user interface 304.

FIG. 4A illustrates that the interactive graphical user interface 304 may display icons 306, 308 representative of other participating mobile device users within a configurable radius or diameter of the primary mobile device 302. An icon 402 representative of the primary mobile device 302 may be displayed in the center of the screen, and icons 306, 308 associated with other mobile devices may be displayed such that they identify the relative distances and directions between the primary mobile device 302 and the other mobile devices. Users may zoom in or out to view smaller or larger geographic areas. The user icons 306, 308 may be superimposed onto a raster map, such as Google® maps. The icons 306, 308 may display different attributes for their associated mobile devices and/or mobile device users. As an example, the icons may identify how important the person is to the conversation. As another example, icons associated with mobile devices in an "available" state may be colored differently than icons 404 associated with user devices in a "Do Not Disturb" state. In an embodiment, the sizes of the rendered icons may be computed on a logarithmic scale so that users in the group communication system who are extremely far away may still be visible on the display.

In an embodiment, the mobile device 302 may be configured to use movement information collected from device sensors (e.g., an accelerometer) to compute directional vectors and update the displayed icons 306, 308 based on the current location, orientation, and/or direction of the mobile device 302. The mobile device may be configured to enable users to select groups of users with which they desire to perform group communications by, for example, drawing a circle 406 around two or more icons 306, 308.

FIG. 4B illustrates an interactive graphical user interface 304 configured to receive user input for creating communication groups in accordance with various embodiments. As mentioned above, the mobile device may be configured to enable users to create and select groups of users with which to initiate a group communication session. A user may create groups of users by, for example, drawing circles 406 around multiple icons/avatars or by specifying a radius or diameter within which devices are to be selected. FIG. 4B illustrates that the circles 406 may be expanded or collapsed to include all mobile devices within a geographic area.

Various embodiments may be best understood by the following sample use cases associated with the top-down perspective graphical display.

In a first top-down perspective use case, the primary mobile device user may be a WORKER whose office is within a few hundred feet of multiple COWORKERS. The interactive graphical user interface of the primary mobile device may display an icon representing WORKER in the middle of the screen, and icons representing each of multiple COWORKERS in proximity to WORKER. Each of the multiple COWORKERS may have set a status (e.g., "Busy," "Available," etc.) that is displayed on the primary mobile device, either as a modification to the user icons (e.g., red to represent busy, green to represent available, etc.) or in addition to the displayed icon (e.g., text above or below the icon, etc.). WORKER may pinch the screen to draw a circle around WORKER's two closest COWORKERS whose status is set to "available," and establish a group communication with the selected COWORKERS.

In a second top-down perspective use case, the primary mobile device user may be a USER standing near the organ pavilion in Balboa Park waiting for the other members of USER's flash mob to arrive. USER may check the primary mobile device to determine that there are only three other people in Balboa Park. USER may zoom out to determine whether there are others still on their way. USER may pinch the screen to create a circle that represents a radius of about 200 feet, and then pinch the screen to create another circle to create a radius of 1,000 feet. USER may send a group communication message to each mobile device within the two circles, notifying them that the dance will start in two minutes and that they need to hurry. USER may monitor the electronic display of the primary mobile device to determine whether the recipients of the group communication message are traveling toward USER's icon and/or if they are likely to reach USER in time for the dance. This may be achieved by viewing the location of the icons relative to the first and second circles.

In a third top-down perspective use case, the primary mobile device user may be a STUDENT in a dining hall who has just secured a dining table after a lengthy wait. STUDENT may check the primary mobile device to determine whether any of his/her friends are entering the dining hall and/or are within the vicinity of the dining hall. STUDENT may select an icon of FIRST FRIEND, and drag the selected icon over an icon of a SECOND FRIEND to initiate a 3-way call with the selected friends (i.e., to inform them he has a table). During the 3-way call, the icons associated with FIRST FRIEND and SECOND FRIEND may be altered (e.g., collage of the two images, etc.) to indicate that they are in a group call.

In a fourth top-down perspective use case, the primary mobile device user may be a USER participating in a group call initiated by an ORIGINATOR by selecting a circled group of icons. The circle of participants may be communicated to, and displayed on, the primary mobile device. USER, having an urgent matter to discuss with another user not participating in the group call, may inform the participants of the group call that USER will be right back, pan the primary mobile device to locate the non-participating user, and click on an icon corresponding to the non-participating user to initiate a direct call. The initiation of the direct call from the primary mobile device may automatically disconnect the previous group call. However, the outline of the circled group of icons representing the participants of the group call may remain active and/or displayed as long as the call continues. After conversing with the non-participating user, USER may select the circled group of icons displayed on the primary mobile device to rejoin the group call.

In a fifth top-down perspective use case, the primary mobile device user may be a USER participating in an important meeting. USER may update the status of the primary mobile device by selecting USER's icon and toggling a status to "Busy." At the conclusion of the meeting, USER may again select USER's icon and move to the next state, such as "Do Not Disturb" or "Available."

In various embodiments, the directionality and modularity of users or groups of users relative to a primary user may be used to modify the operations of a mobile device. In an embodiment, the relative locations of the icons may be determined based on factors other than physical location, such as the importance of an individual to a group conversation, the individual's rank, the individual's logistical relationship to the group, or the individual's functional association with the group.

Figure 5:
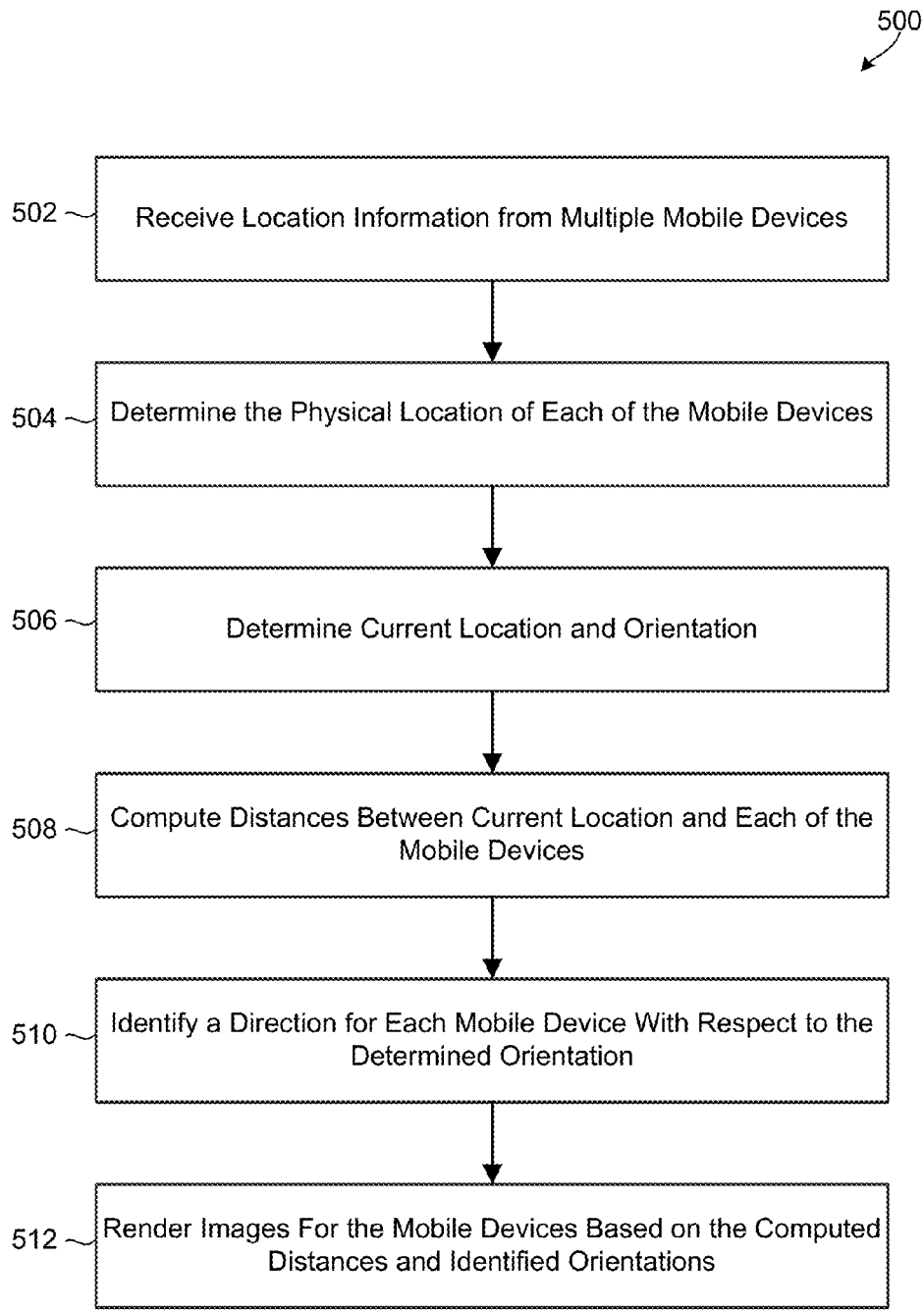
FIG. 5 is a process flow diagram illustrating an embodiment method for rendering images representative of other mobile devices based on the relative directionality, modularity and/or locations of the devices.

FIG. 5 illustrates an embodiment method 500 for rendering images representative of other mobile devices based on the relative directionality, modularity, and/or locations of the devices. In block 502, a mobile device may receive location information from other mobile devices in the communications network. In block 504, the mobile device may use the received location information to determine the physical or geographical location of the other mobile devices. In block 506, the mobile device may determine its current location and orientation. In block 508, the mobile device may compute distances between the current location of the mobile device and the determined locations of the other mobile devices. In block 510, the mobile device may identify the directions to each of the other mobile devices relative to the orientation of the mobile device. In block 512, the mobile device may render images representative of the other mobile devices based on the computed distances and identified orientations.

Figure 6:
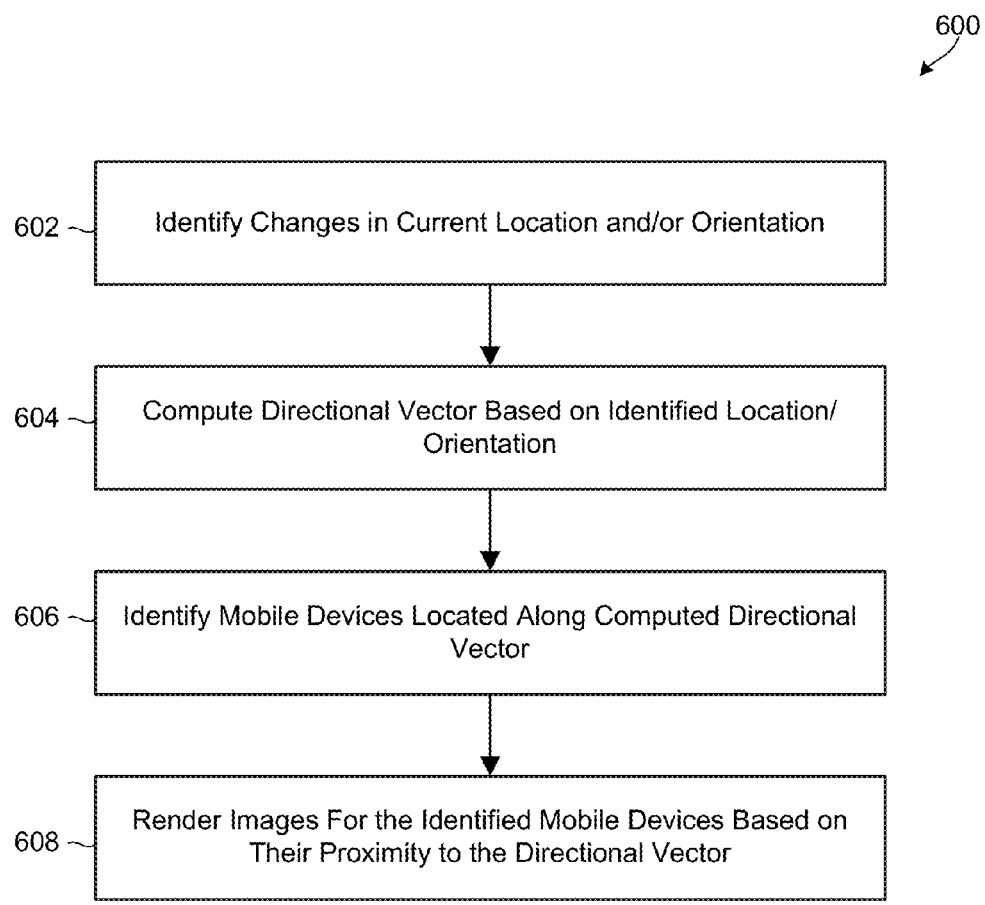
FIG. 6 is a process flow diagram illustrating an embodiment method for updating images representative of other mobile devices based on changes in the relative directionality, modularity and/or locations of one or more mobile devices.

FIG. 6 illustrates an embodiment method 600 for updating images representative of other mobile devices based on changes in the relative directionality, modularity and/or locations of one or more mobile devices. In block 602, the mobile device may identify changes in the current location and/or orientation of the mobile device. In block 604, the mobile device may compute a directional vector based on the identified location and/or orientation of the mobile device. In block 606, the mobile device may identify other mobile devices that are located along the computed directional vector. In block 608, the mobile device may update the display by rendering images for the other mobile device based on their proximity to the computed directional vector.

Figure 7:
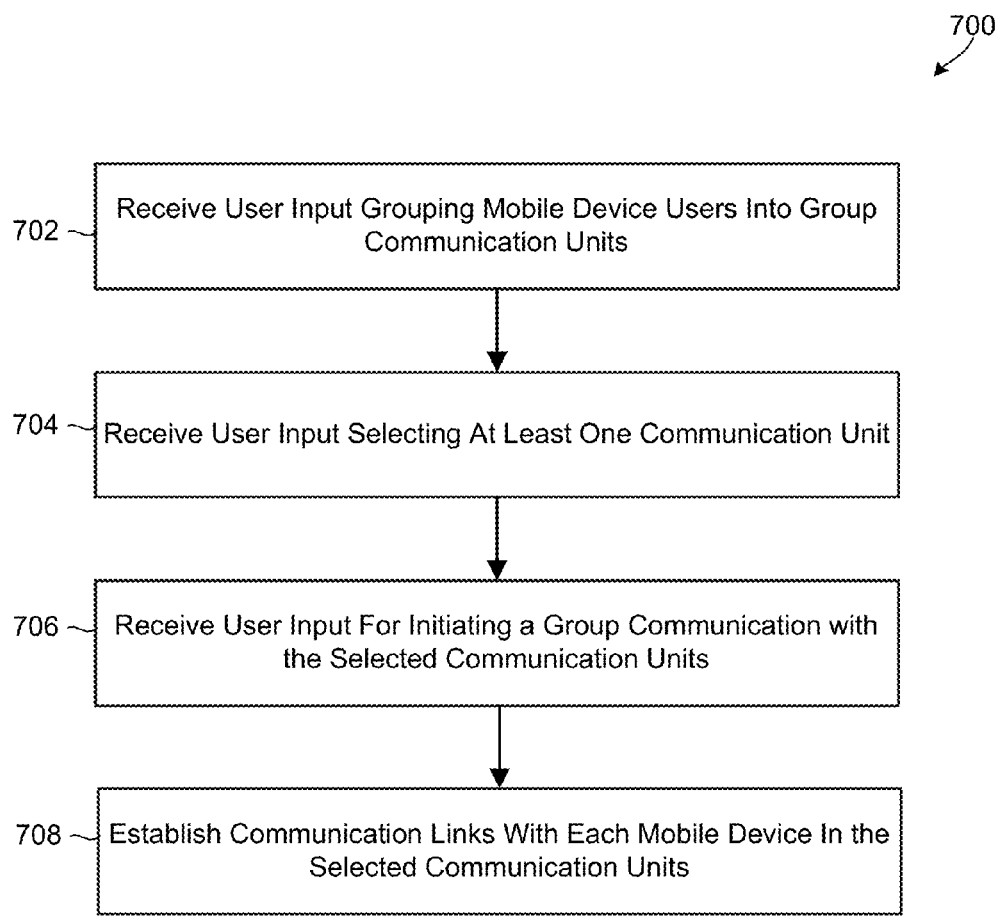
FIG. 7 is a process flow diagram illustrating an embodiment method for establishing group communications with multiple mobile devices based on images representative of other mobile devices.

FIG. 7 illustrates an embodiment method 700 for establishing group communications with multiple mobile devices based on images representative of other mobile devices. In block 702, the mobile device may receive user input grouping other mobile device users into group communication units. In block 704, the mobile device may receive user input selecting at least one communication unit. In block 706, the mobile device may receive user input for initiating a group communication with mobile device users in the selected communication unit. In block 708, the mobile device may establish communication links with each mobile device in the selected communication units.

Various embodiments may include generating a display on a mobile device that is a member of a group communication system by receiving location information associated with each of the devices in the communication system, determining the location of the mobile device, determining a distance between the mobile device and each device, and generating a first-person perspective display. Each of the devices may be represented by an image (e.g., icon, avatar, etc.). The size of each image may be based on the determined distance between the mobile device and that image's associated device. The mobile device may associate a direction vector with the orientation of the mobile device and identify devices located along the direction vector. In an embodiment, only the devices located along the direction vector may be represented by an image on the mobile device screen.

In an embodiment, the mobile device may be configured to determine whether the mobile device has changed orientation, in which case the mobile device may associate a new direction vector with the changed orientation and generate an updated first-person perspective display in which only the devices located along the new direction vector are represented by an image. In an embodiment, the images of mobile devices that are members of the communication group may be displayed differently from images of devices that are not members of the communication group. In an embodiment, only the images of devices in the communication group may be displayed in the first-person perspective. In an embodiment, the mobile device may be configured to receive an indication of a selection of an image, and initiate a communication between the mobile device and the device associated with the selected image.

Various embodiments may include methods for generating a display on a primary mobile device that is a member of a communication system by receiving location information associated with each of the other mobile devices in the communication system, determining the location of the primary mobile device, determining a distance between the primary mobile device and each of the other mobile devices, and generating a top-down perspective display in which an image associated with the primary mobile device appears at the center of the screen. Each of the other mobile devices may be represented by an image positioned around the image of the primary mobile device based on their relative locations and/or positions with respect to the primary mobile device.

In an embodiment, the primary mobile device may be a member of a communication group. The images of the other mobile devices that are members of the communication group may be displayed differently from images of mobile devices that are not members of the communication group. In an embodiment, only the images associated with devices in the communication group may be displayed in the top-down perspective. In an embodiment, the mobile device may be configured to receive a user input selecting a group of images (e.g., a drag of a finger in a circle on the display encompassing the group of images), and initiate a group communication between the primary mobile device and devices associated with the selected group of images. In an embodiment, the indication may be a circle drawn on the display of the mobile device.

Various embodiments may include methods for generating a display on a mobile device that is a member of a communication system by receiving location information associated with each of the devices in the communication system, determining the location of the mobile device, determining a distance between the mobile device and each device, generating a first-person perspective display in which each of the devices may be represented by an image having a size representative of the distance between the mobile device and that avatar's associated device, determining that the mobile device has changed orientation to a horizontal position, and generating a top-down perspective display in which an icon associated with the mobile device appears at the center of the top-down perspective display. Each of the other mobile devices may be represented by an icon positioned on the display based on their relative positions with respect to the mobile device.

Figure 8:
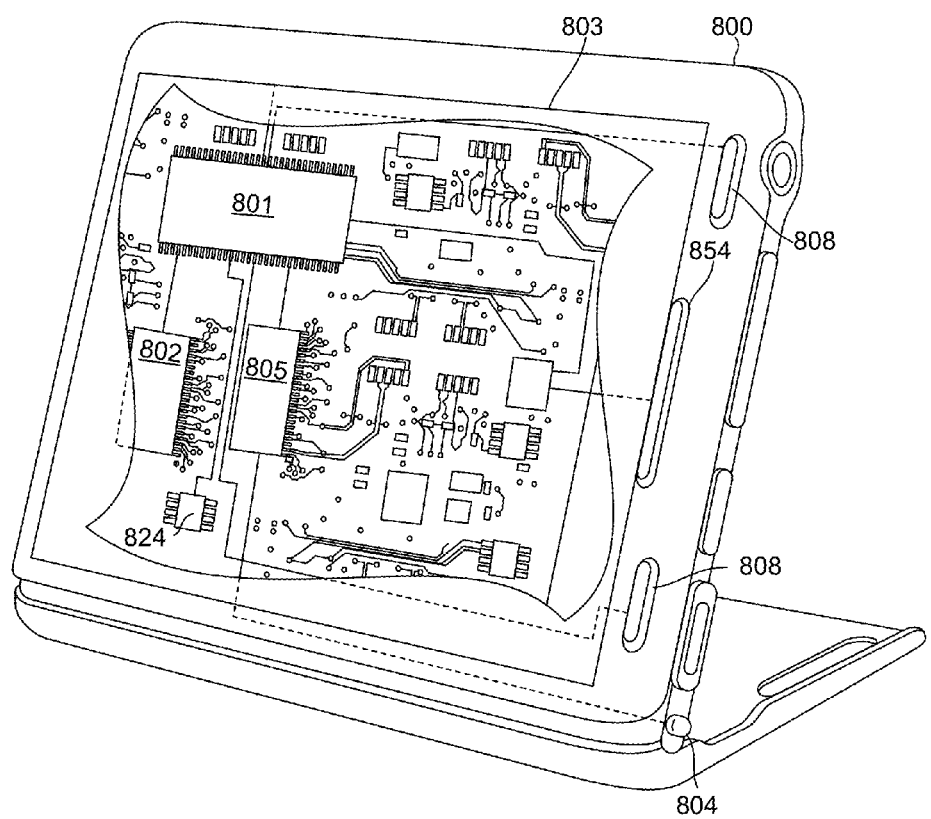
FIG. 8 is a component block diagram of a receiver device suitable for use in an embodiment.

The various embodiments may be implemented on a variety of mobile computing devices, an example of which is illustrated in FIG. 8. Specifically, FIG. 8 is a system block diagram of a mobile device in the form of a phone/smartphone suitable for use with any of the embodiments. A smartphone 800 may include a processor 801 coupled to internal memory 802, a display 803, and to a speaker 854. Additionally, the smartphone 800 may include an antenna 804 for sending and receiving electromagnetic radiation that may be connected to a wireless data link and/or cellular telephone transceiver 805 coupled to the processor 801. Smartphones 800 typically also include menu selection buttons or rocker switches 808 for receiving user inputs.

A typical smartphone 800 also includes a sound encoding/decoding (CODEC) circuit 824 which digitizes sound received from a microphone into data packets suitable for wireless transmission and decodes received sound data packets to generate analog signals that are provided to the speaker 854 to generate sound. Also, one or more of the processor 801, wireless transceiver 805 and CODEC 824 may include a digital signal processor (DSP) circuit (not shown separately). Processing of stored sound to generate filtering criteria may be accomplished by one or more DSP circuits within the components of the smartphone 800 using signal analysis methods is well known in the DSP arts. Also, the application of filtering criteria to suppress undesirable sounds and/or enhance desirable sounds may be accomplished by one or more DSP circuits within the components of the smartphone 800 and/or within the CODEC 824.

Figure 9:
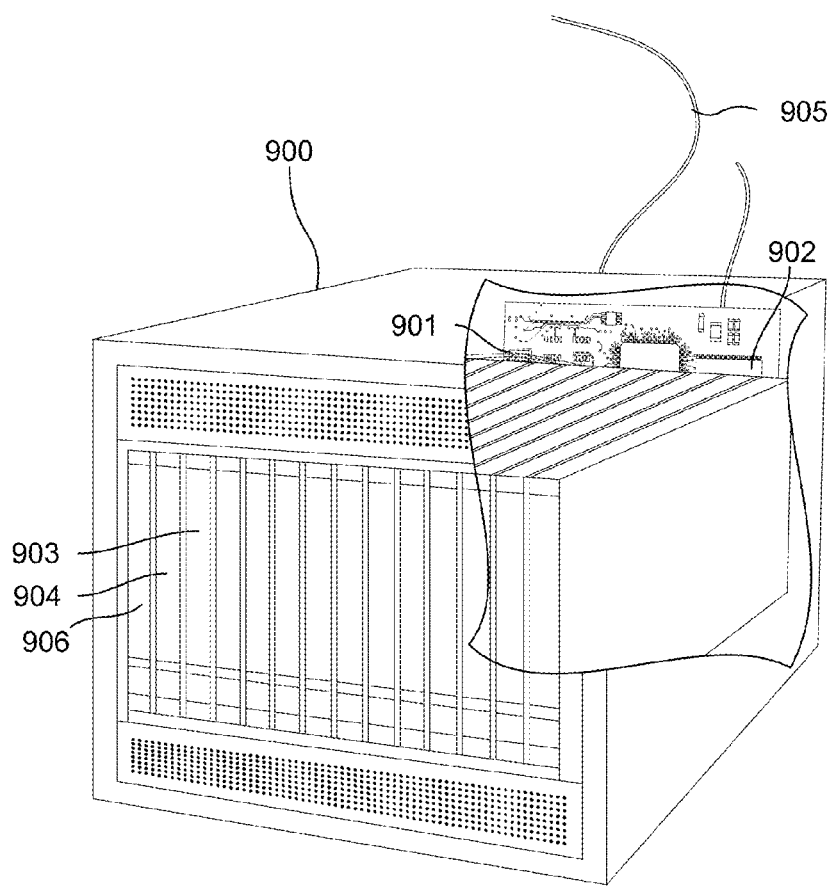
FIG. 9 is a component block diagram of a server device suitable for use in an embodiment.

Various embodiments may be implemented on any of a variety of commercially available server devices, such as the server 900 illustrated in FIG. 9. Such a server 900 typically includes a processor 901 coupled to volatile memory 902 and a large capacity nonvolatile memory, such as a disk drive 903. The server 900 may also include a floppy disc drive, compact disc (CD) or DVD disc drive 906 coupled to the processor 901. The server 900 may also include network access ports 904 coupled to the processor 901 for establishing data connections with a network 905, such as a local area network coupled to other broadcast system computers and servers.

The processors 801, 901 may be any programmable microprocessor, microcomputer or multiple processor chip or chips that can be configured by software instructions (applications) to perform a variety of functions, including the functions of the various embodiments described below. In some mobile receiver devices, multiple processors 901 may be provided, such as one processor dedicated to wireless communication functions and one processor dedicated to running other applications. Typically, software applications may be stored in the internal memory 802, 902, 903 before they are accessed and loaded into the processor 801, 901. The processor 801, 901 may include internal memory sufficient to store the application software instructions.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method for performing group communications comprising:
   receiving on a mobile device location information associated with a plurality of other mobile devices that are members of a communication system;
   determining a location of the mobile device;
   determining an orientation of the mobile device;
   associating a direction vector with the determined orientation of the mobile device;
   identifying at least one of the plurality of other mobile devices located along the direction vector;
   determining a relative distance between the mobile device and each of the plurality of other mobile devices based on the determined location of the mobile device and the location information received from the plurality of other mobile devices;

determining a relative direction of each of the plurality of other mobile devices with respect to the determined orientation of the mobile device;

generating on an electronic display of the mobile device images representative of the plurality of other mobile devices based on the determined relative distance and the determined relative direction by generating a first-person perspective display in which only mobile devices in the plurality of other mobile devices that are located along the direction vector are represented by the images;

receiving a user input via the electronic display;

grouping two or more of the generated images into a communication unit in response to the received user input; and establishing group communications with the communication unit.

2. The method of claim 1, wherein generating on the electronic display of the mobile device images representative of each of the plurality of other mobile devices based on the determined relative distance and the determined relative direction comprises generating the images in sizes indicative of the determined relative distance and the determined relative direction.

3. The method of claim 1, further comprising:
determining whether the mobile device has changed orientation;
associating a new direction vector with the changed orientation of the mobile device; and
generating an updated first-person perspective display in which only mobile devices in the plurality of other mobile devices located along the new direction vector are represented by an image.

4. The method of claim 1, wherein the mobile device is a member of a communication group and images of devices that are members of the communication group are displayed differently from images of devices that are not members of the communication group.

5. The method of claim 1, wherein the mobile device is a member of a communication group and only the images of devices in the communication group are displayed in the first-person perspective display.

6. A computing device, comprising:
means for receiving location information associated with a plurality of mobile devices that are members of a communication system;
means for determining a location of the computing device;
means for determining an orientation of the computing device;
means for associating a direction vector with the determined orientation of the computing device;
means for identifying at least one of the plurality of other mobile devices located along the direction vector;
means for determining a relative distance between the computing device and each of the plurality of mobile devices based on the determined location of the computing device and the location information received from the plurality of mobile devices;
means for determining a relative direction of each of the plurality of mobile devices with respect to the determined orientation of the computing device;
means for generating images representative of the plurality of mobile devices based on the determined relative distance and the determined relative direction comprising means for generating a first-person perspective display in which only mobile devices in the plurality of other mobile devices that are located along the direction vector are represented by the images;

means for receiving a user input via an electronic display;

means for grouping two or more of the generated images into a communication unit in response to the received user input; and means for establishing group communications with the communication unit.

7. The computing device of claim 6, wherein means for generating images representative of each of the plurality of mobile devices based on the determined relative distance and the determined relative direction comprises means for generating the images in sizes indicative of the determined relative distance and the determined relative direction.

8. The computing device of claim 6, further comprising:
means for determining whether the computing device has changed orientation;
means for associating a new direction vector with the changed orientation of the computing device; and
means for generating an updated first-person perspective display in which only devices located along the new direction vector are represented by an image.

9. The computing device of claim 6, further comprising means for associating the computing device with a communication group, wherein means for generating images representative of each of the plurality of mobile devices based on the determined relative distance and the determined relative direction comprises means for displaying images of devices that are members of the communication group differently from images of devices that are not members of the communication group.

10. The computing device of claim 6, further comprising means for associating the computing device with a communication group, wherein means for generating the first-person perspective display in which only devices located along the direction vector are represented by images comprises means for generating the first-person perspective display such that only the images of devices in the communication group are represented by images.

11. A computing device, comprising:
a transceiver;
a memory; and
a processor coupled to the transceiver and the memory, wherein the processor is configured with processor-executable instructions to perform operations comprising:
receiving location information associated with a plurality of mobile devices that are members of a communication system;
determining a location of the computing device;
determining an orientation of the computing device;
associating a direction vector with the determined orientation of the computing device;
identifying at least one of the plurality of other mobile devices located along the direction vector;
determining a relative distance between the computing device and each of the plurality of mobile devices based on the determined location of the computing device and the location information received from the plurality of mobile devices;
determining a relative direction of each of the plurality of mobile devices with respect to the determined orientation of the computing device;
generating images representative of the plurality of mobile devices based on the determined relative distance and the determined relative direction by generating a first-person perspective display in which only mobile devices in the plurality of other mobile devices that are located along the direction vector are represented by the images;

receiving a user input via an electronic display;

grouping two or more of the generated images into a communication unit in response to the received user input; and establishing group communications with the communication unit.

12. The computing device of claim 11, wherein the processor is configured with processor-executable instructions such that generating images representative of each of the plurality of mobile devices based on the determined relative distance and the determined relative direction comprises generating the images in sizes indicative of the determined relative distance and the determined relative direction.

13. The computing device of claim 11, wherein the processor is configured with processor-executable instructions to perform operations further comprising:

determining whether the computing device has changed orientation;

associating a new direction vector with the changed orientation of the computing device; and generating an updated first-person perspective display in which only mobile devices of the plurality of mobile devices that are located along the new direction vector are represented by an image.

14. The computing device of claim 11, wherein the processor is configured with processor-executable instructions to perform operations further comprising associating the computing device with a communication group, and wherein the processor is configured with processor-executable instructions such that generating images representative of each of the plurality of mobile devices based on the determined relative distance and the determined relative direction comprises displaying images of devices that are members of the communication group differently from images of devices that are not members of the communication group.

15. The computing device of claim 11, wherein the processor is configured with processor-executable instructions to perform operations further comprising associating the computing device with a communication group, and wherein the processor is configured with processor-executable instructions such that generating the first-person perspective display in which only mobile devices of the plurality of mobile devices that are located along the direction vector are represented by images comprises generating the first-person perspective display such that only the images of devices in the communication group are displayed in the first-person perspective display.

16. A non-transitory computer readable storage medium having stored thereon processor-executable software instructions configured to cause a processor of a computing device to perform operations comprising:

receiving location information associated with a plurality of mobile devices that are members of a communication system;

determining a location of the computing device;

determining an orientation of the computing device;

associating a direction vector with the determined orientation of the computing device;

identifying at least one of the plurality of other mobile devices located along the direction vector;

determining a relative distance between the computing device and each of the plurality of mobile devices based on the determined location of the computing device and the location information received from the plurality of mobile devices;

determining a relative direction of each of the plurality of mobile devices with respect to the determined orientation of the computing device;

generating images representative of the plurality of mobile devices based on the determined relative distance and the determined relative direction by generating a first-person perspective display in which only mobile devices in the plurality of other mobile devices that are located along the direction vector are represented by the images;

receiving a user input via an electronic display;

grouping two or more of the generated images into a communication unit in response to the received user input; and establishing group communications with the communication unit.

17. The non-transitory computer readable storage medium of claim 16, wherein the stored processor-executable software instructions are configured to cause a processor of a computing device to perform operations such that generating images representative of each of the plurality of mobile devices based on the determined relative distance and the determined relative direction comprises generating the images in sizes indicative of the determined relative distance and the determined relative direction.

18. The non-transitory computer readable storage medium of claim 16, wherein the stored processor-executable software instructions are configured to cause a processor of a computing device to perform operations comprising:

determining whether the computing device has changed orientation;

associating a new direction vector with the changed orientation of the computing device; and generating an updated first-person perspective display in which only mobile devices in the plurality of mobile devices located along the new direction vector are represented by an image.

19. The non-transitory computer readable storage medium of claim 16, wherein the stored processor-executable software instructions are configured to cause a processor of a computing device to perform operations further comprising associating the computing device with a communication group, and wherein the stored processor-executable software instructions are configured to cause a processor of a computing device to perform operations such that generating images representative of each of the plurality of mobile devices based on the determined relative distance and the determined relative direction comprises displaying images of devices that are members of the communication group differently from images of devices that are not members of the communication group.

20. The non-transitory computer readable storage medium of claim 16, wherein the stored processor-executable software instructions are configured to cause a processor of a computing device to perform operations further comprising associating the computing device with a communication group, and wherein the stored processor-executable software instructions are configured to cause a processor of a computing device to perform operations such that generating the first-person perspective display in which only mobile devices in the plurality of mobile devices that are located along the direction vector are represented by images comprises generating the first-person perspective display such that only the images of mobile devices of the plurality of mobile devices that are in the communication group are displayed in the first-person perspective display.

* * * * *